US010253112B2

(12) United States Patent
Chang et al.

(10) Patent No.: US 10,253,112 B2
(45) Date of Patent: Apr. 9, 2019

(54) SOFT SILICONE MEDICAL DEVICES

(71) Applicant: Novartis AG, Basel (CH)

(72) Inventors: Frank Chang, Cumming, GA (US); Troy Vernon Holland, Suwanee, GA (US); Xinming Qian, Johns Creek, GA (US); Robert Scott, Rancho Santa Margarita, CA (US); Joseph Michael Lindacher, Suwanee, GA (US); Uwe Haken, Norcross, GA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/434,101

(22) Filed: Feb. 16, 2017

(65) Prior Publication Data

US 2017/0240658 A1  Aug. 24, 2017

Related U.S. Application Data

(60) Provisional application No. 62/298,127, filed on Feb. 22, 2016.

(51) Int. Cl.
*C08F 2/48* (2006.01)
*A61F 2/16* (2006.01)
*G02B 1/04* (2006.01)

(52) U.S. Cl.
CPC .................. *C08F 2/48* (2013.01); *A61F 2/16* (2013.01); *G02B 1/043* (2013.01); *A61F 2002/16965* (2015.04); *A61F 2240/001* (2013.01)

(58) Field of Classification Search
CPC ........ C08F 2/48; A61F 2/16; A61F 2240/001; A61F 2002/16965; G02B 1/043; G02B 77/20; G02B 77/28
See application file for complete search history.

(56) References Cited

U.S. PATENT DOCUMENTS

| | | |
|---|---|---|
| 3,916,033 A | 10/1975 | Merrill |
| 3,996,187 A | 12/1976 | Travnicek |
| 3,996,189 A | 12/1976 | Travnicek |
| 4,136,250 A | 1/1979 | Mueller et al. |
| 4,153,641 A | 5/1979 | Deichert et al. |
| 4,182,822 A | 1/1980 | Chang et al. |
| 4,189,546 A | 2/1980 | Deichert et al. |
| 4,254,248 A | 3/1981 | Friends et al. |
| 4,259,467 A | 3/1981 | Koegn et al. |
| 4,260,725 A | 4/1981 | Koegn et al. |
| 4,261,875 A | 4/1981 | LeBoeuf |
| 4,276,402 A | 6/1981 | Chromecek et al. |
| 4,327,203 A | 4/1982 | Deichert et al. |
| 4,332,922 A | 6/1982 | Kossmehl et al. |
| 4,341,889 A | 7/1982 | Deichert et al. |
| 4,343,927 A | 8/1982 | Chang et al. |
| 4,355,147 A | 10/1982 | Deichert et al. |
| 4,444,711 A | 4/1984 | Schad |
| 4,460,534 A | 7/1984 | Boehm et al. |
| 4,486,577 A | 12/1984 | Mueller et al. |
| 4,543,398 A | 9/1985 | Angelini et al. |
| 4,605,712 A | 8/1986 | Mueller |
| 4,632,844 A | 12/1986 | Yanagihara et al. |
| 4,661,575 A | 4/1987 | Tom |
| 4,684,538 A | 8/1987 | Klemarczyk |
| 4,703,097 A | 10/1987 | Wingler et al. |
| 4,833,218 A | 5/1989 | Lee |
| 4,837,289 A | 6/1989 | Mueller |
| 4,954,586 A | 9/1990 | Toyoshima et al. |
| 4,954,587 A | 9/1990 | Mueller |
| 5,010,141 A | 4/1991 | Sharma et al. |
| 5,034,461 A | 7/1991 | Lai et al. |
| 5,039,761 A | 8/1991 | Ono et al. |
| 5,070,170 A | 12/1991 | Robertson |
| 5,079,319 A | 1/1992 | Mueller |
| 5,346,946 A | 9/1994 | Yokoyama et al. |
| 5,358,995 A | 10/1994 | Kunzler et al. |
| 5,387,632 A | 2/1995 | Lai et al. |
| 5,416,132 A | 5/1995 | Yokoyama et al. |
| 5,451,617 A | 9/1995 | Lai et al. |
| 5,486,579 A | 1/1996 | Lai et al. |
| 5,760,100 A | 6/1998 | Nicholson et al. |
| 5,843,346 A | 12/1998 | Morrill |
| 5,894,002 A | 4/1999 | Boneberger et al. |
| 5,962,548 A | 10/1999 | Vbanderlaan et al. |
| 5,981,675 A | 11/1999 | Valint et al. |
| 6,039,913 A | 3/2000 | Hirt |
| 6,762,264 B2 | 7/2004 | Kuenzler et al. |
| 6,800,225 B1 | 10/2004 | Hagmann et al. |
| 6,851,805 B2 | 2/2005 | Blum et al. |
| 7,384,590 B2 | 6/2008 | Kelly et al. |
| 7,387,759 B2 | 6/2008 | Kelly et al. |
| 7,490,936 B2 | 2/2009 | Blum et al. |
| 7,605,190 B2 | 10/2009 | Moszner et al. |
| 7,915,323 B2 | 3/2011 | Awasthi et al. |
| 8,154,804 B2 | 4/2012 | McGinn et al. |
| 8,420,711 B2 | 4/2013 | Awasthi et al. |
| 2012/0026457 A1 | 2/2012 | Qui et al. |
| 2012/0029111 A1* | 2/2012 | Chang .................. C08G 77/388 523/107 |

(Continued)

FOREIGN PATENT DOCUMENTS

| | | |
|---|---|---|
| EP | 0632329 A1 | 1/1995 |
| WO | 2017037611 A1 | 3/2017 |

OTHER PUBLICATIONS

Cole et al., "Synthesis and Characterization of Thiol-Ene Functionalized Siloxanes and Evaluation of their Crosslinked Network Properties" J. Polym. Sci. A. Polym. Chem.; 50(20): 4325-4333 (Year: 2012).*

(Continued)

*Primary Examiner* — Jessica M Roswell
(74) *Attorney, Agent, or Firm* — Jian Zhou

(57) ABSTRACT

The invention is related to a method for producing silicone medical devices, in particular, silicone contact lenses, having consistent mechanical properties in a cost-effective manner. The invention is also related to a silicone medical device, especially a soft silicone contact lens.

19 Claims, No Drawings

(56) References Cited

U.S. PATENT DOCUMENTS

| | | |
|---|---|---|
| 2012/0088843 A1 | 4/2012 | Chang et al. |
| 2012/0088844 A1 | 4/2012 | Kuyu et al. |
| 2012/0244088 A1 | 9/2012 | Saxena et al. |
| 2012/0245249 A1 | 9/2012 | Saxena et al. |
| 2017/0068018 A1 | 3/2017 | Qian et al. |

OTHER PUBLICATIONS

Cole et al., "Evaluation of Thiol-Ene Click Chemistry in Functionalize Polysilxoane" J. Polym. A.Polym. Chem.; 51: 1749-1757 (Year: 2013).*

Kade, et al.; "The Power of Thiol-ene Chemistry"; Journal of Polymer Science: Part A: Polymer Chemistry, vol. 48, 2010, pp. 743-750.

Metters, et al.; "Network Formation and Degradation Behavior of Hydrogels Formed by Michael-Type Addition Reactions"; Biomacromolecules, American Chemical Society, vol. 6, No. 1, 2005, pp. 290-301.

Lee, et al.; "Thiol-Allyl Ether-Methacrylate Ternary Systems. Polymerization Mechanism"; Macromolecules; American chemical Society; vol. 40, No. 5, 2007, pp. 1466-1472.

Cramer, et al.; "Mechanism and Modeling of a Thiol-Ene Photopolymerization"; Macromolecules; American Chemical Society; vol. 36; No. 12; 2003; pp. 4631-4636.

Mueller, et al.; "Photocrosslinking of Silicones. Part 13. Photoinduced Thiol-Ene Crosslinking of Modified Silicones"; Journal of Macromolecular Science; Pure Appl. Chem., 1996; A33(4), pp. 439-457.

Schlogl, et al.; "Photo-vulcanization using thiol-ene chemistry: Film formation, morphology and network characteristics of UV crosslinked rubber latices"; Polymer, 55; 2014; pp. 5584-5595.

* cited by examiner

SOFT SILICONE MEDICAL DEVICES

This application claims the benefits under 35 USC § 119 (e) of U.S. provisional application No. 62/298,127 filed 22 Feb. 2016, herein incorporated by reference in its entirety.

The present invention generally relates to a method for producing soft silicone medical devices, especially soft silicone contact lenses with consistent mechanical properties. In addition, the present invention provides medical devices (especially soft silicone contact lenses) having desired and consistent mechanical properties.

BACKGROUND

Cornea cannot receive oxygen from the blood supply like other tissue. When the eye is open, the cornea primarily receives oxygen from the atmosphere, via the tears. When the eye is closed (e.g., during sleep), the cornea receives oxygen mainly from oxygen diffusion from the capillary plexus of the upper palpebral aperture vasculature. If sufficient oxygen does not reach the cornea, corneal swelling occurs. Extended periods of oxygen deprivation cause the undesirable growth of blood vessels in the cornea. Wearing of a soft contact lens inevitably reduces the oxygen supply to the cornea, because it can form an oxygen barrier that prevents oxygen from reaching the cornea. The oxygen transmissibility (Dk/t) of the contact lens worn by a patient, depending upon the oxygen permeability (Dk) of the lens material and the thickness (t) of the contact lens, is of vital importance for the oxygen supply to the cornea either from the atmosphere in the open eye state or from the capillary plexus of the upper palpebral aperture vasculature.

In recent years, soft silicone hydrogel contact lenses become more and more popular because of their high oxygen transmissibility and comfort. Silicone hydrogel (SiHy) contact lenses are made of a hydrated, crosslinked polymeric material that contains silicone and from about 10% to about 80% by weight of water within the lens polymer matrix at equilibrium. However, a SiHy contact lens may not have a very high oxygen permeability (e.g., greater than 180 Barrers). A very high oxygen permeability is likely required for alleviating the adverse effect of oxygen-impermeable electro-optic elements, which are incorporated in contact lenses (see, U.S. Pat. Nos. 6,851,805, 7,490,936 and 8,154,804), upon the permeation of oxygen through the contact lenses.

Silicone contact lenses, made essentially of a crosslinked silicone polymer (or a silicone rubber or elastomer), have been proposed previously (U.S. Pat. Nos. 3,916,033; 3,996,187, 3,996,189; 4,332,922; and 4,632,844, herein incorporated by references in their entireties), because of their very high oxygen permeability and good mechanical and optical properties. However, crosslinked silicone polymers generally are produced by crosslinking a silicone composition comprising (1) at least one polydiorganosiloxane having at least two alkenyl groups (e.g., vinyl group, allyl group, 1-propenyl group, and isopropenyl group) each bonded to the silicon atom of a siloxane unit, (2) at least one hydride-containing polydiorganosiloxane having at least two silane groups (one hydrogen atom bonded to the silicon atom of a siloxane unit), and (3) a hydrosilylation catalyst (e.g., a platinum group metal or its compounds), according to hydrosilylation reaction. This hydrosilylation crosslinking (curing) approach has several disadvantages. First, hydrosilylation crosslinking requires relatively long reaction time and thereby lower the production yield. Second, hydrosilylation reaction is performed at an elevated temperature with extended hours. If silicone contact lenses are produced by cast-molding in disposable plastic molds (e.g., polypropylene molds) in a mass-production manner currently used in contact lens industry for producing hydrogel or silicone hydrogel contact lenses, the harsh curing conditions (e.g., high temperature and extended hours) may cause significant issues in lens metrology. Third, the mechanical properties of silicone contact lenses are quit sensitive to the stoichiometry of silane and alkenyl groups in a silicone composition. It would be difficult to control this stoichiometry and to provide silicone contact lenses with adequate and consistent mechanical properties. Fourth, it would be a challenge to remove the hydrosilylation catalyst post molding so as to minimize or eliminate any toxicological risk.

Therefore, there is still a need for a method for producing silicone contact lenses having consistent mechanical properties in a cost-effective manner. There is also a need for silicone contact lenses with desired and consistent mechanical properties.

SUMMARY OF THE INVENTION

In one aspect, the invention provides a method for producing a silicone medical device (especially a soft silicone contact lens), the method of invention comprising the steps of: (1) obtaining a polymerizable silicone composition which comprises (a) from about 65% to about 95% by weight of one or more first polydiorganosiloxanes each having at least two (meth)acryloyl groups and an averaged molecular weight of at least about 2000 Daltons, (b) from about 1.0% to about 20.0% by weight of one or more second polydiorganosiloxanes each having at least two thiol groups and an averaged molecular weight of at least about 2000 Daltons, and (c) from about 0.1% to about 3% by weight of a free-radical initiator, provided that components (a) to (c) listed above and any additional polymerizable components present in the polymerizable silicone composition add up to 100% by weight; (2) introducing the polymerizable silicone composition into a mold for making a silicone medical device (preferably a silicone contact lens); and (3) curing thermally or actinically the polymerizable silicone composition in the mold to form the silicone medical device (preferably the silicone contact lens), wherein the formed silicone medical device (preferably the formed silicone contact lens) has an elastic modulus of about 1.2 MPa or less and an elongation at break of about 200% or larger.

In another aspect, the invention provides a medical device (especially a soft contact lens), comprising or consisting essentially of a crosslinked silicone material, wherein the crosslinked silicone material comprises: (a) repeating units of at least one first polydiorganosiloxane having at least two (meth)acryloyl groups; and (b) repeating units of at least one second polydiorganosiloxane having at least two thiol groups, wherein the medical device (preferably the silicone contact lens) has an elastic modulus of about 1.2 MPa or less and an elongation at break of about 200% or larger.

These and other aspects of the invention will become apparent from the following description of the presently preferred embodiments. The detailed description is merely illustrative of the invention and does not limit the scope of the invention, which is defined by the appended claims and equivalents thereof. As would be obvious to one skilled in the art, many variations and modifications of the invention may be effected without departing from the spirit and scope of the novel concepts of the disclosure.

DETAILED DESCRIPTION OF EMBODIMENTS OF THE INVENTION

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well-known and commonly employed in the art.

A "medical device", as used herein, refers to a device having surfaces that contact tissue, blood, or other bodily fluids of patients in the course of their operation or utility. Exemplary medical devices include: (1) extracorporeal devices for use in surgery such as blood oxygenators, blood pumps, blood sensors, tubing used to carry blood and the like which contact blood which is then returned to the patient; (2) prostheses implanted in a human or animal body such as vascular grafts, stents, pacemaker leads, heart valves, and the like that are implanted in blood vessels or in the heart; (3) devices for temporary intravascular use such as catheters, guide wires, and the like which are placed into blood vessels or the heart for purposes of monitoring or repair; (4) artificial tissues such as artificial skin for burn patients; (5) dentifices, dental moldings; (6) ophthalmic devices (e.g., intraocular lenses, contact lenses, corneal onlay, stents, glaucoma shunt, or the like). In a preferred embodiment, medical devices are ophthalmic devices; and (7) cases or containers for storing ophthalmic devices or ophthalmic solutions. In a preferred embodiment, medical devices are ophthalmic devices.

"Contact Lens" refers to a structure that can be placed on or within a wearer's eye. A contact lens can correct, improve, or alter a user's eyesight, but that need not be the case.

A "silicone contact lens" refers to a contact lens made of a crosslinked silicone material as its bulk (or core or base) material which has three-dimensional polymer networks (i.e., polymer matrix), is insoluble in water, and can hold less than about 7.5% (preferably less than about 5%, more preferably less than about 2.5%, even more preferably less than about 1%) by weight of water when fully hydrated.

A "hydrogel" or "hydrogel material" refers to a crosslinked polymeric material which has three-dimensional polymer networks (i.e., polymer matrix), is insoluble in water, and can hold at least 10 percent by weight of water in its polymer matrix when it is fully hydrated.

A "silicone hydrogel" refers to a hydrogel or hydrogel material which comprises silicone.

As used in this application, the term "non-silicone hydrogel" refers to a hydrogel that is theoretically free of silicon.

The term "soluble", in reference to a compound or material in a solvent, means that the compound or material can be dissolved in the solvent to give a solution with a concentration of at least about 0.1% by weight at room temperature (i.e., a temperature of about 22° C. to about 28° C.).

The term "insoluble", in reference to a compound or material in a solvent, means that the compound or material can be dissolved in the solvent to give a solution with a concentration of less than 0.005% by weight at room temperature (as defined above).

As used in this application, the term "actinically-crosslinkable group" is employed herein in a broad sense and is intended to encompass any groups that can participate in free-radical polymerization reaction. Examples of actinically-crosslinkable groups are ethylenically unsaturated groups and thiol group (—SH).

As used in this application, the term "ethylenically unsaturated group" refers to any groups containing at least one >C=C< group. Exemplary ethylenically unsaturated groups include without limitation (meth)acryloyl

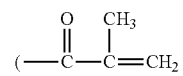

and/or

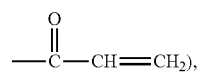

allyl, vinyl, styrenyl, or other C=C containing groups. Exemplary (meth)acryloyl groups include acryloyloxy group, methacryloyloxy group, acryloylamido group, methacryloylamido group, and combinations thereof.

As used in this application, the term "polymerizable component" in reference to a polymerizable silicone composition means any component other than a free-radical initiator that is present in the polymer silicone composition and can participate in free-radical polymerization reaction.

The term "(meth)acryloylamido group" refers to a radical of

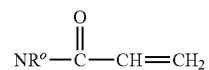

and/or

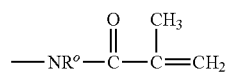

in which $R^o$ is hydrogen or a $C_1$-$C_6$ alkyl.

The term "(meth)acryloyloxy group" refers to a radical of

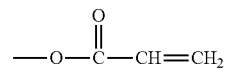

and/or

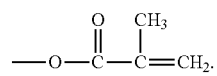

The term "(meth)acrylamide" refers to methacrylamide and/or acrylamide.

The term "(meth)acrylate" refers to methacrylate and/or acrylate.

As used herein, "actinically" in reference to curing, crosslinking or polymerizing of a polymerizable composition, a prepolymer or a material means that the curing (e.g., crosslinked and/or polymerized) is performed by actinic irradiation, such as, for example, UV/visible irradiation, ionizing radiation (e.g. gamma ray or X-ray irradiation), microwave irradiation, and the like. Thermal curing or actinic curing methods are well-known to a person skilled in the art.

A "monomer" refers to a compound that contains one or more crosslinkable groups and has an average molecular weight of 700 Daltons or less.

A "macromer" or "prepolymer" refers to a compound or polymer that contains one or more crosslinkable groups and has an average molecular weight of greater than 700 Daltons.

A "vinylic monomer" refers to a compound that has one sole ethylenically unsaturated group and is soluble in a solvent.

A "hydrophilic vinylic monomer", as used herein, refers to a vinylic monomer which as a homopolymer typically yields a polymer that is water-soluble or can absorb at least 10 percent by weight water.

A "hydrophobic vinylic monomer", as used herein, refers to a vinylic monomer which as a homopolymer typically yields a polymer that is insoluble in water and can absorb less than 10 percent by weight water.

A "vinylic crossliking agent" refers to a compound with two or more ethylenically unsaturated groups.

As used in this application, the term "polymer" means a material formed by polymerizing/crosslinking one or more monomers or macromers or prepolymers or combinations thereof.

As used in this application, the term "molecular weight" or "averaged molecular weight" of a polymeric material (including monomeric or macromeric materials) refers to the number-average molecular weight unless otherwise specifically noted or unless testing conditions indicate otherwise.

A "polydiorganosiloxane" refers to a compound containing a polymeric segment of

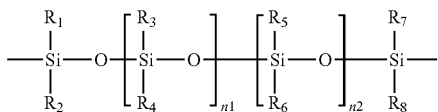

in which n1 and n2 independently of each other are an integer of from 0 to 500 and (n1+n2) is from 10 to 500, $R_1$, $R_2$, $R_3$, $R_4$, $R_5$, $R_6$, $R_7$, and $R_8$ independently of one another, are $C_1$-$C_{10}$ alkyl, $C_1$-$C_4$ alkyl- or $C_1$-$C_4$-alkoxy-substituted phenyl, $C_1$-$C_{10}$ fluoroalkyl, $C_1$-$C_{10}$ fluoroether, or $C_6$-$C_{18}$ aryl radical. Where all the segments in the compound are polydimethylsiloxane segments

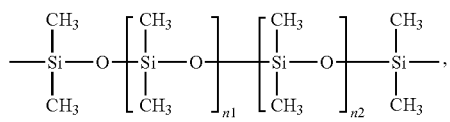

the compound is a polydimethylsiloxane.

The term "fluid" as used herein indicates that a material is capable of flowing like a liquid.

The term "alkyl" refers to a monovalent radical obtained by removing a hydrogen atom from a linear or branched alkane compound. An alkyl group (radical) forms one bond with one other group in an organic compound.

The term "alkylene divalent group" or "alkylene diradical" or "alkyl diradical" interchangeably refers to a divalent radical obtained by removing one hydrogen atom from an alkyl. An alkylene divalent group forms two bonds with other groups in an organic compound.

The term "alkyl triradical" refers to a trivalent radical obtained by removing two hydrogen atoms from an alkyl. An alkyl triradical forms three bonds with other groups in an organic compound.

The term "alkoxy" or "alkoxyl" refers to a monovalent radical obtained by removing the hydrogen atom from the hydroxyl group of a linear or branched alkyl alcohol. An alkoxy group (radical) forms one bond with one other group in an organic compound.

In this application, the term "substituted" in reference to an alkyl diradical (i.e., alkylene divalent radical) or an alkyl radical means that the alkyl diradical or the alkyl radical comprises at least one substituent which replaces one hydrogen atom of the alkyl diradical or the alkyl radical and is selected from the group consisting of hydroxy (—OH), carboxy (—COOH), —$NH_2$, sulfhydryl (—SH), $C_1$-$C_4$ alkyl, $C_1$-$C_4$ alkoxy, $C_1$-$C_4$ alkylthio (alkyl sulfide), $C_1$-$C_4$ acylamino, $C_1$-$C_4$ alkylamino, di-$C_1$-$C_4$ alkylamino, halogen atom (Br or Cl), and combinations thereof.

A free radical initiator can be either a photoinitiator or a thermal initiator. A "photoinitiator" refers to a chemical that initiates free radical crosslinking/polymerizing reaction by the use of light. A "thermal initiator" refers to a chemical that initiates radical crosslinking/polymerizing reaction by the use of heat energy.

The intrinsic "oxygen permeability", Dk, of a material is the rate at which oxygen will pass through a material. As used in this application, the term "oxygen permeability (Dk)" in reference to a hydrogel (silicone or non-silicone) or a contact lens means a measured oxygen permeability (Dk) which is corrected for the surface resistance to oxygen flux caused by the boundary layer effect according to the procedures described in Example 1 of 2012/0026457 A1 (herein incorporated by reference in its entirety). Oxygen permeability is conventionally expressed in units of barrers, where "barrer" is defined as [($cm^3$ oxygen)(mm)/($cm^2$)(sec)(mm Hg)]×$10^{-10}$.

The "oxygen transmissibility", Dk/t, of a lens or material is the rate at which oxygen will pass through a specific lens or material with an average thickness of t [in units of mm] over the area being measured. Oxygen transmissibility is conventionally expressed in units of barrers/mm, where "barrers/mm" is defined as [($cm^3$ oxygen)/($cm^2$)(sec)(mm Hg)]×$10^{-9}$.

The term "modulus" or "elastic modulus" in reference to a contact lens or a material means the tensile modulus or Young's modulus which is a measure of the stiffness of a contact lens or a material. The modulus can be measured using a method in accordance with ANSI Z80.20 standard. A person skilled in the art knows well how to determine the elastic modulus of a silicone hydrogel material or a contact lens. For example, all commercial contact lenses have reported values of elastic modulus.

The invention is generally related to silicone medical devices (in particular, silicone contact lenses) having consistent mechanical properties and to cost-efficient methods for producing such silicone medical device (in particular, such silicone contact lenses).

In one aspect, the invention provides a method for producing a silicone medical device (especially a soft silicone contact lens), the method of invention comprising the steps of:
(1) obtaining a polymerizable silicone composition which comprises
   (a) from about 65% to about 99% (preferably from about 70% to about 97%, more preferably from about 75% to about 95%, even more preferably from about 80% to about 93%) by weight of (i) one or more first polydiorganosiloxanes each having at least two (meth)acryloylamido groups, (ii) one or more second polydiorganosiloxanes each having at least two (meth)acryloyloxy groups, or (iii) a mixture thereof, wherein each of the first and second polydiorganosiloxanes has an averaged molecular weight of at least about 2000 Daltons (preferably at least about 4000 Dalton, more preferably at least about 6000 Daltons, even more preferably from about 6000 to about 200000 Daltons),
   (b) from about 1.0% to about 20.0% (preferably from about 2% to about 15%, more preferably from about 3% to about 10%, even more preferably from about 4% to about 7%) by weight of one or more third polydiorganosiloxanes each having at least two thiol groups and an averaged molecular weight of at least about 2000 Daltons (preferably at least about 3000 Dalton, more preferably at least about 4000 Daltons, even more preferably from about 4000 to about 150000 Daltons), and
   (c) from about 0.1% to about 3% (preferably from about 0.2% to about 2.5%, more preferably from about 0.5% to about 2%, even more preferably from about 0.75% to about 1.5%) by weight of a free-radical initiator,
   provided that components (a) to (c) listed above and any additional polymerizable components present in the polymerizable silicone composition add up to 100% by weight;
(2) introducing the polymerizable silicone composition into a mold for making a silicone medical device (preferably a silicone contact lens); and
(3) curing thermally or actinically the polymerizable silicone composition in the mold to form the silicone medical device (preferably the silicone contact lens),
wherein the formed silicone medical device (preferably the formed silicone contact lens) has an elastic modulus of about 1.2 MPa or less (preferably about 1.1 MPa or less, more preferably from about 0.2 MPa to about 1.0 MPa, even more preferably from about 0.3 MPa to about 0.9 MPa) and an elongation at break of about 200% or larger (preferably about 250% or larger, more preferably about 300% or larger, even more preferably about 350% or larger).

In a preferred embodiment, the medical device is a silicone contact lens.

In accordance with the invention, polydiorganosiloxanes with (meth)acryloyl or thiol groups can be linear or branched, preferably be linear. The (meth)acryloyl and thiol groups can be terminal groups or pendant groups or both. A linear polydiorganosiloxane with (meth)acryloylamido, (meth)acryloyloxy, or thiol groups can be a polydiorganosiloxane comprising two or more polydiorganosiloxane segments linked via a linkage between each pair of polydirganosiloxane segments (or so-called chain-extended polydiorganosiloxane). α,ω-bis(thiolpropyl)-polydimethylsiloxane Any suitable polydiorganosiloxanes with (meth)acryloylamido, (meth)acryloyloxy, or thiol groups can be used in the invention. Preferred examples of such polydiorganosiloxanes are α,ω-bis(methacryloylamido)-terminated polydimethylsiloxanes of various molecular weights, α,ω-bis(acryloylamido)-terminated polydimethylsiloxanes of various molecular weights, α,ω-bis(methacryloyloxy)-terminated polydimethylsiloxanes of various molecular weights, α,ω-bis(acryloyloxy)-terminated polydimethylsiloxanes of various molecular weights, α,ω-bis(mercapto)-terminated polydimethylsiloxanes of various molecular weights, polydiorganosiloxanes disclosed in US (herein incorporated by reference in its entirety); chain-extended polysiloxane vinylic crosslinkers disclosed in US201008843A1 and US20120088844A1 (herein incorporated by references in their entireties); the reaction products of glycidyl methacrylate with amino-functional polydimethylsiloxanes; polysiloxane-containing macromers disclosed in U.S. Pat. Nos. 4,136,250, 4,153,641, 4,182,822, 4,189,546, 4,259,467, 4,260,725, 4,261,875, 4,343,927, 4,254,248, 4,355,147, 4,276,402, 4,327,203, 4,341,889, 4,486,577, 4,543,398, 4,605,712, 4,661,575, 4,684,538, 4,703,097, 4,833,218, 4,837,289, 4,954,586, 4,954,587, 5,010,141, 5,034,461, 5,070,170, 5,079,319, 5,039,761, 5,346,946, 5,358,995, 5,387,632, 5,416,132, 5,451,617, 5,486,579, 5,760,100, 5,962,548, 5,981,675, 6,039,913, and 6,762,264 and in U.S. Pat. Appl. Pub. Nos. 201008843A1 and 20120088844A1 (here incorporated by reference in their entireties).

Examples of suitable thermal initiators include, but are not limited to, 2,2'-azobis (2,4-dimethylpentanenitrile), 2,2'-azobis (2-methylpropanenitrile), 2,2'-azobis (2-methylbutanenitrile), peroxides such as benzoyl peroxide, and the like. Preferably, the thermal initiator is 2,2'-azobis(isobutyronitrile) (AIBN).

Suitable photoinitiators are benzoin methyl ether, diethoxyacetophenone, a benzoylphosphine oxide, 1-hydroxycyclohexyl phenyl ketone and Darocur and Irgacur types, preferably Darocur 1173® and Darocur 2959®, Germane-based Norrish Type I photoinitiators. Examples of benzoylphosphine initiators include 2,4,6-trimethylbenzoyl-diphenylophosphine oxide; bis-(2,6-dichlorobenzoyl)-4-N-propylphenylphosphine oxide; and bis-(2,6-dichlorobenzoyl)-4-N-butylphenylphosphine oxide. Reactive photoinitiators which can be incorporated, for example, into a macromer or can be used as a special monomer are also suitable. Examples of reactive photoinitiators are those disclosed in EP 632 329, herein incorporated by reference in its entirety. The polymerization can then be triggered off by actinic radiation, for example light, in particular UV light of a suitable wavelength. The spectral requirements can be controlled accordingly, if appropriate, by addition of suitable photosensitizers.

A polymerizable silicone composition can further comprise one or more polymerizable components selected from the group consisting of a silicone-containing vinylic monomer, a hydrophobic vinylic monomer, a hydrophilic vinylic monomer, a vinylic crosslinking agent, a UV-absorbing vinylic monomer, and combinations thereof. Preferred examples of a silicone-containing vinylic monomer, a hydrophobic vinylic monomer, a hydrophilic vinylic monomer, a vinylic crosslinking agent, and a UV-absorbing vinylic monomer are described below. It should be understood that the total amount of those components in a polymerizable silicone composition should be about 15% or less.

Any suitable silicone-containing vinylic monomers can be used in the invention. Examples of preferred silicone-containing vinylic monomers include without limitation N-[tris(trimethylsiloxy)silylpropyl]-(meth)acrylamide, N-[tris(dimethylpropylsiloxy)-silylpropyl]-(meth)acrylamide, N-[tris(dimethylphenylsiloxy)silylpropyl](meth)acrylamide, N-[tris(dimethylethylsiloxy)silylpropyl](meth)acrylamide, N-(2-hydroxy-3-(3-(bis(trimethylsilyloxy)methylsilyl)propyloxy)propyl)-2-methyl acrylamide; N-(2-hydroxy-3-(3-(bis(trimethylsilyloxy)methylsilyl)propyloxy) propyl) acrylamide; N,N-bis[2-hydroxy-3-(3-(bis(trimethylsilyloxy)methylsilyl)propyloxy)propyl]-2-methyl acrylamide; N,N-bis[2-hydroxy-3-(3-(bis(trimethylsilyloxy)methylsilyl)propyloxy)propyl]acrylamide; N-(2-hydroxy-3-(3-(tris(trimethylsilyloxy)silyl)propyloxy)propyl)-2-methyl acrylamide; N-(2-hydroxy-3-(3-(tris(trimethylsilyloxy)silyl)propyloxy)propyl)acrylamide; N,N-bis[2-hydroxy-3-(3-(tris(trimethylsilyloxy)silyl)propyloxy)propyl]-2-methyl acrylamide; N,N-bis[2-hydroxy-3-(3-(tris(trimethylsilyloxy)silyl)propyloxy)propyl]acrylamide; N-[2-hydroxy-3-(3-(t-butyldimethylsilyl)propyloxy)propyl]-2-methyl acrylamide; N-[2-hydroxy-3-(3-(t-butyldimethylsilyl)propyloxy)propyl]acrylamide; N,N-bis[2-hydroxy-3-(3-(t-butyldimethylsilyl)propyloxy)propyl]-2-methyl acrylamide; N,N-bis[2-hydroxy-3-(3-(t-butyldimethylsilyl)propyloxy)propyl]acrylamide; 3-methacryloxy propylpentamethyldisiloxane, trimethylsilylmethyl(meth)acrylate, pentamethyldisiloxyethyl (meth)acrylate, tris(trimethylsiloxy)silylpropyl (meth)acrylate, methyldi(trimethylsiloxy)methyldisiloxanylpropyl(meth)acrylate, tert-butyltetramethyldisiloxanylethyl(meth)acrylate, (3-methacryloxy-2-hydroxypropyloxy)propylbis(trimethylsiloxy)methylsilane), (3-methacryloxy-2-hydroxypropyloxy)propyltris(trimethylsiloxy)silane, 3-methacryloxy-2-(2-hydroxyethoxy)-propyloxy)propylbis(trimethylsiloxy)methylsilane, N-2-methacryloxyethyl-O-(methyl-bis-trimethylsiloxy-3-propyl)silyl carbamate, 3-(trimethylsilyl)propylvinyl carbonate, 3-(vinyloxycarbonylthio)propyl-tris(trimethyl-siloxy)silane, 3-[tris(trimethylsiloxy)silyl]propylvinyl carbamate, 3-[tris(trimethylsiloxy)silyl]propyl allyl carbamate, 3-[tris(trimethylsiloxy)silyl]propyl vinyl carbonate, t-butyldimethyl-siloxyethyl vinyl carbonate; trimethylsilylethyl vinyl carbonate, and trimethylsilylmethyl vinyl carbonate); monomethacrylated or monoacrylated polydimethylsiloxanes of various molecular weight (e.g., mono-3-methacryloxypropyl terminated, mono-butyl terminated polydimethylsiloxane or mono-(3-methacryloxy-2-hydroxypropyloxy) propyl terminated, mono-butyl terminated polydimethylsiloxane); mono-vinyl carbonate-terminated polydimethylsiloxanes; mono-vinyl carbamate-terminated polydimethylsiloxane; mono-methacrylamide-terminated polydimethylsiloxanes; mono-acrylamide-terminated polydimethylsiloxanes; carbosiloxane vinylic monomers disclosed in U.S. Pat. Nos. 7,915,323 and 8,420,711, in US Patent Application Publication Nos. 2012/244088 and 2012/245249 (herein incorporated by references in their entireties); combinations thereof.

Examples of preferred hydrophobic vinylic monomers include methylacrylate, ethyl-acrylate, propylacrylate, isopropylacrylate, cyclohexylacrylate, 2-ethylhexylacrylate, methylmethacrylate, ethylmethacrylate, propylmethacrylate, vinyl acetate, vinyl propionate, vinyl butyrate, vinyl valerate, styrene, chloroprene, vinyl chloride, vinylidene chloride, acrylonitrile, 1-butene, butadiene, methacrylonitrile, vinyl toluene, vinyl ethyl ether, perfluorohexylethyl-thio-carbonyl-aminoethyl-methacrylate, isobornyl methacrylate, trifluoroethyl methacrylate, hexafluoro-isopropyl methacrylate, hexafluorobutyl methacrylate.

Any suitable hydrophilic vinylic monomers can be used in the invention. Examples of preferred vinylic monomers include without limitation N,N-dimethylacrylamide (DMA), N,N-dimethylmethacrylamide (DMMA), 2-acrylamidoglycolic acid, N-hydroxypropylacrylamide, N-hydroxyethyl acrylamide, N-[tris(hydroxymethyl)methyl]-acrylamide, N-vinyl pyrrolidone, N-vinyl formamide, N-vinyl acetamide, N-vinyl isopropylamide, N-vinyl-N-methyl acetamide, N-methyl-3-methylene-2-pyrrolidone, 1-methyl-5-methylene-2-pyrrolidone, 5-methyl-3-methylene-2-pyrrolidone, 2-hydroxyethylmethacrylate (HEMA), 2-hydroxyethyl acrylate (HEA), hydroxypropyl acrylate, hydroxypropyl methacrylate (HPMA), trimethylammonium 2-hydroxy propylmethacrylate hydrochloride, aminopropyl methacrylate hydrochloride, di methylaminoethyl methacrylate (DMAEMA), glycerol methacrylate (GMA), a $C_1$-$C_4$-alkoxy polyethylene glycol (meth)acrylate having a weight average molecular weight of up to 1500, (meth)acrylic acid, and mixtures thereof. In accordance with the invention, a polymerizable silicone composition comprises less than 5% (preferably less than 4%, more preferably about 3% or less, even more preferably about 2% or less) by weight of one or more hydrophilic vinylic monomers listed above.

Examples of preferred vinylic cross-linking agents include without limitation tetraethyleneglycol diacrylate, triethyleneglycol diacrylate, diethyleneglycol diacrylate, ethyleneglycol diacrylate, tetraethyleneglycol dimethacrylate, triethyleneglycol dimethacrylate, diethyleneglycol dimethacrylate, ethyleneglycol dimethacrylate, tetraethyleneglycol divinyl ether, triethyleneglycol divinyl ether, diethyleneglycol divinyl ether, ethyleneglycol divinyl ether, trimethylopropane trimethacrylate, pentaerythritol tetramethacrylate, bisphenol A dimethacrylate, vinyl methacrylate, ethylenediamine dimethyacrylamide, ethylenediamine diacrylamide, glycerol dimethacrylate, triallyl isocyanurate, triallyl cyanurate, allylmethacrylate, allylacrylate, N-allyl-methacrylamide, N-allyl-acrylamide, 1,3-bis(methacrylamidopropyl)-1,1,3,3-tetrakis-(trimethylsiloxy)disiloxane, N,N'-methylenebisacrylamide, N,N'-methylenebismethacrylamide, N,N'-ethylenebisacrylamide, N,N'-ethylenebismethacrylamide, 1,3-bis(N-methacrylamidopropyl)-1,1,3,3-tetrakis-(trimethylsiloxy)disiloxane, 1,3-bis(methacrylamidobutyl)-1,1,3,3-tetrakis-(trimethylsiloxy)disiloxane, 1,3-bis(acrylamidopropyl)-1,1,3,3-tetrakis(trimethylsiloxy)disiloxane, 1,3-bis(methacryloxyethylureidopropyl)-1,1,3,3-tetrakis(trimethylsiloxy)disiloxane, and combinations thereof. The amount of a cross-linking agent used is expressed in the weight content with respect to the total polymer and is preferably less than 2%, and more preferably from about 0.01% to about 1%.

Any suitable UV-absorbing vinylic monomers can be used in a polymerizable composition for preparing a polymer of the invention. Examples of preferred UV-absorbing and UV/HEVL-absorbing, benzotriazole-containing vinylic monomers include without limitation: 2-(2-hydroxy-5-vinylphenyl)-2H-benzotriazole, 2-(2-hydroxy-5-acrylyloxyphenyl)-2H-benzotriazole, 2-(2-hydroxy-3-methacrylamido methyl-5-tert octylphenyl)benzotriazole, 2-(2'-hydroxy-5'-methacrylamidophenyl)-5-chlorobenzotriazole, 2-(2'-hydroxy-5'-methacrylamidophenyl)-5-methoxybenzotriazole, 2-(2'-hydroxy-5'-methacryloxypropyl-3'-t-butyl-phenyl)-5-chlorobenzotriazole, 2-(2'-hydroxy-5'-methacryloxypropylphenyl)benzotriazole, 2-hydroxy-5-methoxy-3-(5-(trifluoromethyl)-2H-benzo[d][1,2,3]triazol-2-yl)benzyl methacrylate (WL-1), 2-hydroxy-5-methoxy-3-(5-methoxy-2H-benzo[d][1,2,3]triazol-2-yl)benzyl methacrylate (WL-5), 3-(5-fluoro-2H-benzo[d][1,2,3]triazol-2-yl)-2-hydroxy-5-methoxybenzyl methacrylate (WL-2), 3-(2H-benzo[d][1,2,3]triazol-2-yl)-2-hydroxy-5-methoxybenzyl methacrylate (WL-3), 3-(5-chloro-2H-benzo[d][1,2,3]triazol-2-yl)-2-hydroxy-5-methoxybenzyl methacrylate (WL-4), 2-hydroxy-5-methoxy-3-(5-methyl-2H-benzo[d][1,2,3]triazol-2-yl)benzyl methacrylate (WL-6), 2-hydroxy-5-methyl-3-(5-(trifluoromethyl)-2H-benzo[d][1,2,3]triazol-2-yl)benzyl methacrylate (WL-7), 4-allyl-2-(5-chloro-2H-benzo[d][1,2,3]triazol-2-yl)-6-methoxyphenol (WL-8), 2-{2'-Hydroxy-3'-tert-5-[3"-(4"-vinylbenzyloxy)propoxy]phenyl}-5-methoxy-2H-benzotriazole, phenol, 2-(5-chloro-2H-benzotriazol-2-yl)-6-(1,1-dimethylethyl)-4-ethenyl- (UVAM), 2-(2'-hydroxy-5'-methacryloxyethyl phenyl) benzotriazole (2-Propenoic acid, 2-methyl-, 2-[3-(2H-benzotriazol-2-yl)-4-hydroxyphenyl]ethyl ester, Norbloc), 2-{2'-Hydroxy-3'-tert-butyl-5'-[3'-methacryloyloxypropoxy]phenyl}-5-methoxy-2H-benzotriazole (UV13), 2-[2'-Hydroxy-3'-tert-butyl-5'-(3'-acryloyloxypropoxy)phenyl]-5-trifluoromethyl-2H-benzotriazole (C F$_3$-UV13), 2-(2'-hydroxy-5-methacrylamidophenyl)-5-methoxybenzotriazole (UV6), 2-(3-allyl-2-hydroxy-5-methylphenyl)-2H-benzotriazole (UV9), 2-(2-Hydroxy-3-methallyl-5-methyl-phenyl)-2H-benzotriazole (UV12), 2-3'-t-butyl-2'-hydroxy-5'-(3"-dimethylvinylsilylpropoxy)-2'-hydroxy-phenyl)-5-methoxybenzotriazole (UV15), 2-(2'-hydroxy-5'-methacryloylpropyl-3'-tert-butyl-phenyl)-5-methoxy-2H-benzotriazole (UV16), 2-(2'-hydroxy-5'-acryloylpropyl-3'-tert-butyl-phenyl)-5-methoxy-2H-benzotriazole (UV16A), 2-Methylacrylic acid 3-[3-tert-butyl-5-(5-chlorobenzotriazol-2-yl)-4-hydroxyphenyl]-propyl ester (16-100, CAS#96478-15-8), 2-(3-(tert-butyl)-4-hydroxy-5-(5-methoxy-2H-benzo[d][1,2,3]triazol-2-yl)phenoxy)ethyl methacrylate (16-102); Phenol, 2-(5-chloro-2H-benzotriazol-2-yl)-6-methoxy-4-(2-propen-1-yl) (CAS#1260141-20-5); 2-[2-Hydroxy-5-[3-(methacryloyloxy)propyl]-3-tert-butylphenyl]-5-chloro-2H-benzotriazole; 2-(3'-tert-butyl-2'-hydroxy-5'-(3"-methacryloyloxypropoxy)phenyl)-5-chloro-2H-benzotriazole; 2-(3'-tert-butyl-2'-hydroxy-5'-(3"-methacryloyloxypropoxy)phenyl)-2H-benzotriazole. In accordance with the invention, the polymerizable composition comprises about 0.2% to about 5.0%, preferably about 0.3% to about 2.5%, more preferably about 0.5% to about 1.8%, by weight of a UV-absorbing agent.

Where a vinylic monomer capable of absorbing ultraviolet radiation and high energy violet light (HEVL) is used in the invention, a Germane-based Norrish Type I photoinitiator and a light source including a light in the region of about 400 to about 550 nm are preferably used to initiate a free-radical polymerization. Any Germane-based Norrish Type I photoinitiators can be used in this invention, so long as they are capable of initiating a free-radical polymerization under irradiation with a light source including a light in the region of about 400 to about 550 nm. Examples of Germane-based Norrish Type I photoinitiators are acylgermanium compounds described in U.S. Pat. No. 7,605,190 (herein incorporated by reference in its entirety). Preferably, the monomer of lens-forming materials comprises at least one of the following acylgermanium compounds.

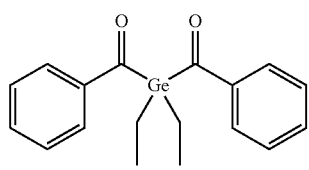

-continued

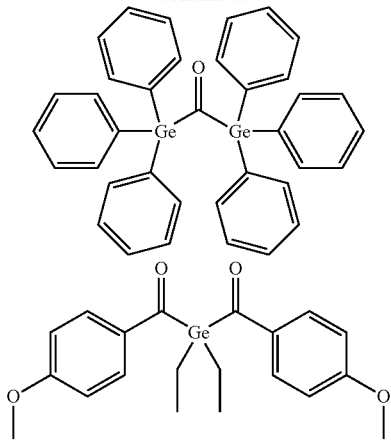

In accordance with the invention, a polymerizable silicone composition can be a solution or a melt at a temperature from about 20° C. to about 85° C. Preferably, a polymerizable silicone composition is a solution of all desirable components in a suitable solvent, or a mixture of suitable solvents. More preferably, a polymerizable silicone composition is a solventless mixture.

A polymerizable silicone composition can be prepared by blending all the desirable components homogeneously, or by dissolving all of the desirable components in any suitable solvent, such as, water, a mixture of water and one or more organic solvents miscible with water, an organic solvent, or a mixture of one or more organic solvents, as known to a person skilled in the art.

Example of preferred organic solvents includes without limitation, tetrahydrofuran, tripropylene glycol methyl ether, dipropylene glycol methyl ether, ethylene glycol n-butyl ether, ketones (e.g., acetone, methyl ethyl ketone, etc.), diethylene glycol n-butyl ether, diethylene glycol methyl ether, ethylene glycol phenyl ether, propylene glycol methyl ether, propylene glycol methyl ether acetate, dipropylene glycol methyl ether acetate, propylene glycol n-propyl ether, dipropylene glycol n-propyl ether, tripropylene glycol n-butyl ether, propylene glycol n-butyl ether, dipropylene glycol n-butyl ether, tripropylene glycol n-butyl ether, propylene glycol phenyl ether dipropylene glycol dimethyl ether, polyethylene glycols, polypropylene glycols, ethyl acetate, butyl acetate, amyl acetate, methyl lactate, ethyl lactate, i-propyl lactate, methylene chloride, 2-butanol, 1-propanol, 2-propanol, menthol, cyclohexanol, cyclopentanol and exonorborneol, 2-pentanol, 3-pentanol, 2-hexanol, 3-hexanol, 3-methyl-2-butanol, 2-heptanol, 2-octanol, 2-nonanol, 2-decanol, 3-octanol, norborneol, tert-butanol, tert-amyl alcohol, 2-methyl-2-pentanol, 2,3-dimethyl-2-butanol, 3-methyl-3-pentanol, 1-methylcyclohexanol, 2-methyl-2-hexanol, 3,7-dimethyl-3-octanol, 1-chloro-2-methyl-2-propanol, 2-methyl-2-heptanol, 2-methyl-2-octanol, 2-2-methyl-2-nonanol, 2-methyl-2-decanol, 3-methyl-3-hexanol, 3-methyl-3-heptanol, 4-methyl-4-heptanol, 3-methyl-3-octanol, 4-methyl-4-octanol, 3-methyl-3-nonanol, 4-methyl-4-nonanol, 3-methyl-3-octanol, 3-ethyl-3-hexanol, 3-methyl-3-heptanol, 4-ethyl-4-heptanol, 4-propyl-4-heptanol, 4-isopropyl-4-heptanol, 2,4-dimethyl-2-pentanol, 1-methylcyclopentanol, 1-ethylcyclopentanol, 1-ethylcyclopentanol, 3-hydroxy-3-methyl-1-butene, 4-hydroxy-4-methyl-1-cyclopentanol, 2-phenyl-2-propanol, 2-methoxy-2-methyl-2-propanol 2,3,4-trimethyl-3-pentanol, 3,7-dimethyl-3-octanol, 2-phenyl-2-butanol, 2-methyl-1-phenyl-2-propanol and 3-ethyl-3-pentanol, 1-ethoxy-2-propanol, 1-methyl-2-propanol, t-amyl alcohol, isopropanol, 1-methyl-2-pyrrolidone, N,N-dimethylpropionamide, dimethyl formamide, dimethyl acetamide, dimethyl propionamide, N-methyl pyrrolidinone, and mixtures thereof.

A polymerizable silicone composition can be cured thermally or actinically as known to a person skilled in the art.

Lens molds for making contact lenses (or medical devices) are well known to a person skilled in the art and, for example, are employed in cast molding or spin casting. For example, a mold (for cast molding) generally comprises at least two mold sections (or portions) or mold halves, i.e. first and second mold halves. The first mold half defines a first molding (or optical) surface and the second mold half defines a second molding (or optical) surface. The first and second mold halves are configured to receive each other such that a lens forming cavity is formed between the first molding surface and the second molding surface. The molding surface of a mold half is the cavity-forming surface of the mold and in direct contact with lens-forming material.

Methods of manufacturing mold sections for cast-molding a contact lens are generally well known to those of ordinary skill in the art. The process of the present invention is not limited to any particular method of forming a mold. In fact, any method of forming a mold can be used in the present invention. The first and second mold halves can be formed through various techniques, such as injection molding or lathing. Examples of suitable processes for forming the mold halves are disclosed in U.S. Pat. No. 4,444,711 to Schad; U.S. Pat. No. 4,460,534 to Boehm et al.; U.S. Pat. No. 5,843,346 to Morrill; and U.S. Pat. No. 5,894,002 to Boneberger et al., which are also incorporated herein by reference.

Virtually all materials known in the art for making molds can be used to make molds for making contact lenses. For example, polymeric materials, such as polyethylene, polypropylene, polystyrene, PMMA, Topas® COC grade 8007-S10 (clear amorphous copolymer of ethylene and norbornene, from Ticona GmbH of Frankfurt, Germany and Summit, N.J.), or the like can be used. Other materials that allow UV light transmission could be used, such as quartz glass and sapphire.

In a preferred embodiment, reusable molds are used and the polymerizable silicone composition is cured actinically under a spatial limitation of actinic radiation to form a silicone contact lens. Examples of preferred reusable molds are those disclosed in U.S. Pat. Nos. 6,800,225, 7,384,590, and 7,387,759, which are incorporated by reference in their entireties. Reusable molds can be made of quartz, glass, sapphire, $CaF_2$, a cyclic olefin copolymer (such as for example, Topas® COC grade 8007-S10 (clear amorphous copolymer of ethylene and norbornene) from Ticona GmbH of Frankfurt, Germany and Summit, N.J., Zeonex® and Zeonor® from Zeon Chemicals LP, Louisville, Ky.), polymethylmethacrylate (PMMA), polyoxymethylene from DuPont (Delrin), Ultem® (polyetherimide) from G.E. Plastics, PrimoSpire®, etc.

In accordance with the invention, the polymerizable silicone composition can be introduced (dispensed) into a cavity formed by a mold according to any known methods.

After the polymerizable silicone composition is dispensed into the mold, it is crosslinked or polymerized (i.e., cured) to produce a contact lens (or a medical device). Crosslinking or polymerizing may be initiated thermally or actinically, preferably by exposing the lens-forming composition in the mold to a spatial limitation of actinic radiation to crosslink the polymerizable components in the polymerizable composition.

Opening of the mold so that the molded article can be removed from the mold may take place in a manner known per se.

The molded contact lens (or substrate) can be subject to extraction to remove unpolymerized polymerizable components. The extraction solvent can be any solvent known to a person skilled in the art. Examples of suitable extraction solvent are those described above.

Thereafter, for example, in the cast molding manufacturing method, the lens (or substrate) may be released from the mold and subjected to post-molding processes, such as, extraction, hydration, surface modification, packaging, autoclave, etc., as known to a person skilled in the art.

Lens packages (or containers) are well known to a person skilled in the art for autoclaving and storing a soft contact lens (a medical device). Any lens (or device) packages can be used in the invention. Preferably, a lens (or device) package is a blister package which comprises a base and a cover, wherein the cover is detachably sealed to the base, wherein the base includes a cavity for receiving a sterile packaging solution and the contact lens (or medical device).

Lenses (devices) are packaged in individual packages, sealed, and sterilized (e.g., by autoclave at about 120° C. or higher for at least about 30 minutes under pressure) prior to dispensing to users. A person skilled in the art will understand well how to seal and sterilize lens (or device) packages.

In accordance with the invention, a packaging solution contains at least one buffering agent and one or more other ingredients known to a person skilled in the art. Examples of other ingredients include without limitation, tonicity agents, surfactants, antibacterial agents, preservatives, and lubricants (e.g., cellulose derivatives, polyvinyl alcohol, polyvinyl pyrrolidone).

The packaging solution contains a buffering agent in an amount sufficient to maintain a pH of the packaging solution in the desired range, for example, preferably in a physiologically acceptable range of about 6.5 to about 7.5. Any known, physiologically compatible buffering agents can be used. Suitable buffering agents as a constituent of the contact lens care composition according to the invention are known to the person skilled in the art. Examples are boric acid, borates, e.g. sodium borate, citric acid, citrates, e.g. potassium citrate, bicarbonates, e.g. sodium bicarbonate, TRIS (2-amino-2-hydroxymethyl-1,3-propanediol), Bis-Tris (Bis-(2-hydroxyethyl)-imino-tris-(hydroxymethyl)-methane), bis-aminopolyols, triethanolamine, ACES (N-(2-hydroxyethyl)-2-aminoethanesulfonic acid), BES (N,N-Bis(2-hydroxyethyl)-2-aminoethanesulfonic acid), HEPES (4-(2-hydroxyethyl)-1-piperazineethanesulfonic acid), MES (2-(N-morpholino)ethanesulfonic acid), MOPS (3-[N-morpholino]-propanesulfonic acid), PIPES (piperazine-N, N'-bis(2-ethanesulfonic acid), TES (N-[Tris (hydroxymethyl)methyl]-2-aminoethanesulfonic acid), salts thereof, phosphate buffers, e.g. $Na_2HPO_4$, $NaH_2PO_4$, and $KH_2PO_4$ or mixtures thereof. A preferred bis-aminopolyol is 1,3-bis(tris[hydroxymethyl]-methylamino)propane (bis-TRIS-propane). The amount of each buffer agent in a packaging solution is preferably from 0.001% to 2%, preferably from 0.01% to 1%; most preferably from about 0.05% to about 0.30% by weight.

The packaging solution has a tonicity of from about 200 to about 450 milliosmol (mOsm), preferably from about 250 to about 350 mOsm. The tonicity of a packaging solution can be adjusted by adding organic or inorganic substances which affect the tonicity. Suitable occularly acceptable tonicity agents include, but are not limited to sodium chloride, potassium chloride, glycerol, propylene glycol, polyols, mannitols, sorbitol, xylitol and mixtures thereof.

A packaging solution of the invention has a viscosity of from about 1 centipoise to about 8 centipoises, more preferably from about 1.2 centipoises to about 5 centipoises, at 25° C.

In another aspect, the invention provides a medical device (especially a soft contact lens), comprising or consisting essentially of a crosslinked silicone material, wherein the crosslinked silicone material comprises: (a) repeating units of at least one first polydiorganosiloxane having at least two (meth)acryloyl groups; and (b) repeating units of at least one second polydiorganosiloxane having at least two thiol groups, wherein the medical device (preferably the silicone contact lens) has an elastic modulus of about 1.2 MPa (preferably about 1.1 MPa or less, more preferably from about 0.2 MPa to about 1.0 MPa, even more preferably from about 0.3 MPa to about 0.9 MPa) and an elongation at break of about 200% or larger (preferably about 250% or larger, more preferably about 300% or larger, even more preferably about 350% or larger).

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part or can be combined in any manner and/or used together, as illustrated below:

1. A medical device comprising a crosslinked silicone material, wherein the crosslinked silicone material comprises: (a) repeating units of a first polydiorganosiloxane having at least two (meth)acryloyl groups; and (b) repeating units of a second polydiorganosiloxane having at least two thiol groups; wherein the medical device has an elastic modulus of about 1.2 MPa or less and an elongation at break of about 200% or larger.
2. The medical device of invention 1, wherein the first polydiorganosiloxane has an average molecular weight of at least about 2000 Daltons (preferably at least about 4000 Dalton, more preferably at least about 6000 Daltons, even more preferably from about 6000 to about 200000 Daltons).
3. The medical device of invention 1 or 2, wherein the second polydiorganosiloxane has an average molecular weight of at least about 2000 Daltons (preferably at least about 3000 Dalton, more preferably at least about 4000 Daltons, even more preferably from about 4000 to about 150000 Daltons).
4. The medical device of any one of inventions 1 to 3, wherein the first polydiorganosiloxane is a linear polydiorganosiloxane.
5. The medical device of invention 4, wherein the first polydiorganosiloxane is a linear polydimethylsiloxane.
6. The medical device of any one of inventions 1 to 5, wherein the second polydiorganosiloxane is a linear polydiorganosiloxane.
7. The medical device of invention 6, wherein the second polydiorganosiloxane is a linear polydimethylsiloxane.
8. The medical device of any one of invention 1 to 7, wherein the first polydiorganosiloxane comprises at least two acryloylamido groups.
9. The medical device of any one of invention 1 to 7, wherein the first polydiorganosiloxane comprises at least two methacryloylamido groups.
10. The medical device of any one of inventions 1 to 7, wherein the first polydiorganosiloxane comprises at least two methacryloylamido groups, wherein the crosslinked silicone material further comprises repeating units of at least one third polydiorganosiloxane having at least two (meth)acryloyloxy groups.
11. The medical device of any one of inventions 1 to 7, the first polydiorganosiloxane comprises at least two acryloylamido groups, wherein the crosslinked silicone material further comprises repeating units of at least one third polydiorganosiloxane having at least two (meth)acryloyloxy groups.
12. The medical device of invention 10 or 11, wherein the third polydiorganosiloxane has an average molecular weight of at least about 2000 Daltons (preferably at least about 4000 Dalton, more preferably at least about 6000 Daltons, even more preferably from about 6000 to about 200000 Daltons).
13. The medical device of any one of inventions 10 to 12, wherein the third polydiorganosiloxane comprises at least two acryloyloxy groups.
14. The medical device of any one of inventions 10 to 12, wherein the third polydiorganosiloxane comprises at least two methacryloyloxy groups.
15. The medical device of any one of inventions 10 to 14, wherein the third polydiorganosiloxane is a linear polydiorganosiloxane.
16. The medical device of invention 15, wherein the third polydiorganosiloxane is a linear polydimethylsiloxane.
17. The medical device of any one of inventions 1 to 7, wherein the first polydiorganosiloxane comprises at least two acryloyloxy groups.
18. The medical device of any one of inventions 1 to 7, wherein the first polydiorganosiloxane comprises at least two methacryloyloxy groups.
19. The medical device of any one of inventions 1 to 18, wherein the crosslinked silicone material further comprises repeating units of at least UV-absorbing vinylic monomer.
20. The medical device of any one of inventions 1 to 19, wherein the medical device is a silicone intraocular lens or a silicone contact lens.
21. The medical device of invention 20, wherein the medical device is a silicone contact lens.
22. The medical device of any one of inventions 1 to 21, wherein the medical device has an elastic modulus of about 1.1 MPa or less (preferably from about 0.2 MPa to about 1.0 MPa, more preferably from about 0.3 MPa to about 0.9 MPa).
23. The medical device of any one of inventions 1 to 22, wherein the medical device has an elongation at break of about 250% or larger (preferably about 300% or larger, more preferably about 350% or larger).
24. A method for producing a silicone medical device, comprising the steps of:
    (1) obtaining a polymerizable silicone composition which comprises
       (a) from about 65% to about 98.9% by weight of (i) one or more first polydiorganosiloxanes each having at least two (meth)acryloylamido groups, (ii) one or more second polydiorganosiloxanes each having at least two (meth)acryloyloxy groups, or (iii) a mixture thereof, wherein each of the first and second polydiorganosiloxanes has an averaged molecular weight of at least about 2000 Daltons, (b) from about 1.0% to about 20.0% by weight of one or more third polydiorganosiloxanes each having at least two thiol groups and an averaged molecular weight of at least about 2000 Daltons, and (c) from about 0.1% to about 3% by weight of a free-radical initiator, provided that components (a) to (c) listed above and any additional polymerizable components present in the polymerizable silicone composition add up to 100% by weight;

(2) introducing the polymerizable silicone composition into a mold for making a silicone medical device; and (3) curing thermally or actinically the polymerizable silicone composition in the mold to form the silicone medical device, wherein the formed silicone medical device has an elastic modulus of about 1.2 MPa or less and an elongation at break of about 200% or larger.

25. The method of invention 24, wherein the polymerizable silicone composition comprises from about 70% to about 97% (preferably from about 75% to about 95%, more preferably from about 80% to about 93%) by weight of the first polydiorganosiloxanes.

26. The method of invention 24, wherein the polymerizable silicone composition comprises from about 70% to about 97% (preferably from about 75% to about 95%, more preferably from about 80% to about 93%) by weight of the second polydiorganosiloxanes.

27. The method of invention 24, wherein the polymerizable silicone composition comprises from about 70% to about 97% (preferably from about 75% to about 95%, more preferably from about 80% to about 93%) by weight of a mixture of the first and second polydiorganosiloxanes.

28. The method of any one of inventions 24 to 27, wherein the first and second polydiorganosiloxanes independent of one another have an average molecular weight of at least about 4000 Dalton (preferably at least about 6000 Daltons, more preferably from about 6000 to about 200000 Daltons).

29. The method of any one of inventions 24 to 28, wherein the first, second and third polydiorganosiloxanes independent of one another are a linear polydiorganosiloxane.

30. The method of invention 29, wherein the first, second and third polydiorganosiloxanes independent of one another are a linear polydimethylsiloxane.

31. The method of any one of inventions 24 to 30, wherein the polymerizable silicone composition comprises from about 2% to about 15% (preferably from about 3% to about 10%, more preferably from about 4% to about 7%) by weight of one or more second polydiorganosiloxanes.

32. The method of any one of inventions 24 to 31, wherein the third polydiorganosiloxanes have an average molecular weight of at least about 3000 Dalton (preferably at least about 4000 Daltons, more preferably from about 4000 to about 150000 Daltons).

33. The method of any one of inventions 24 to 32, wherein the polymerizable silicone composition comprises from about 0.2% to about 2.5% (preferably from about 0.5% to about 2%, more preferably from about 0.75% to about 1.5%) by weight of a free-radical initiator.

34. The method of any one of inventions 24 to 33, wherein the free-radical initiator is a thermal initiator.

35. The method of any one of inventions 24 to 33, wherein the free-radical initiator is a photoinitiator.

36. The method of any one of inventions 24 to 35, wherein the polymerizable silicone composition comprises a UV-absorbing vinylic monomer.

37. The method of any one of inventions 24 to 36, wherein the medical device is a silicone intraocular lens or a silicone contact lens.

38. The method of invention 37, wherein the medical device is a silicone contact lens.

39. The method of any one of inventions 24 to 38, wherein the medical device has an elastic modulus of about 1.1 MPa or less (preferably from about 0.2 MPa to about 1.0 M Pa, more preferably from about 0.3 MPa to about 0.9 MPa).

40. The method of any one of inventions 24 to 39, wherein the medical device has an elongation at break of about 250% or larger (preferably about 300% or larger, more preferably about 350% or larger).

The previous disclosure will enable one having ordinary skill in the art to practice the invention. Various modifications, variations, and combinations can be made to the various embodiment described herein. In order to better enable the reader to understand specific embodiments and the advantages thereof, reference to the following examples is suggested. It is intended that the specification and examples be considered as exemplary.

EXAMPLE 1

Photo-rhelogy of Formulation

Photo-rheology data are measured using the Hamamatsu lamp with a 330 nm high pass cutoff filter placed just before the sample. The UV source is a Hamamatsu UV lamp manufactured by Hamamatsu K.K. Light from the source is passed down a light guide and through a 330 nm cut-off filter manufactured by Dünnschicht Technik GmbH Germany, before being impinged on the sample contained between a quartz plate and the rheology probe.

The intensity of light that passes through the optical plate is measured by an ESE detector that weighs the intensity to the master spectrum of 1% Darocure 1173.

Oxygen Permeability Measurements

Oxygen and ion permeability measurements are carried out with lenses after extraction and autoclave in phosphate buffered saline (PBS) at 120° C. for 45 min.

The apparent oxygen permeability ($Dk_{app}$), the apparent oxygen transmissibility (Dk/t), the intrinsic (or edge-corrected) oxygen permeability ($Dk_c$) of a lens and a lens material are determined according to procedures described in Example 1 of U.S. patent application publication No. 2012/0026457 A1 (herein incorporated by reference in its entirety).

Lens Elastic Modulus and Elongation at Break

Lens elastic modulus and elongation at break were measured using an MTS Insight mechanical testing apparatus. Lenses were cut into approximately 6.5 mm gauge strips and center thickness measured using a Rehder Electronic Thickness Gauge. Lenses were then loaded onto mechanical grips and measured in a custom load cell containing phosphate buffered saline equilibrated at 21+/-2° C.

Lens Swelling Rate in Solvent

Lens swelling rate is determined by measuring lens diameter. The lens diameter is obtained by using Optimec® Limited. The lens diameters at dry state and at equilibrium in solvent are to be used to calculate the lens swelling rate in solvent. Swelling ratio=(lens diameter in a solvent—lens diameter in dry state)/lens diameter in dry state.

% Water of Lens

Lenses are blotted between two layers of lint free blotting cloth and placed on an aluminum weigh pan. The hydrated weight is recorded and then the lenses are placed in a vacuum oven at 23° C., for 24 hours, at 99 mbar. Afterward, the dry weight is taken. Water content is measured by comparing the hydrated lens weight with the dry weight.

EXAMPLE 2

A phosphate buffered saline (PBS) is prepared by dissolving $NaH_2PO_4.H_2O$, $Na_2HPO_4.2H_2O$, and in a given volume of purified water (distilled or deionized) to have the following composition: about 0.044 w/w % $NaH_2PO_4.H_2O$, about 0.388 w/w/% $Na_2HPO_4.2H_2O$, and about 0.79 w/w % NaCl.

Soft silicone contact lenses are produced by photopolymerization of a polymerizable silicone composition in plastic molds. A clear composition is prepared to have 99% by weight of α,ω-bis(diacrylamidopropyl)-polydimethylsiloxane (Mw~7500) and 1% by weight of a photoinitiator Darocur® 1173 (Ciba). Photo-rheology study is carried out to determine cure time and the shear storage modulus (kPa). The shear storage modulus (G') is 459 kPa and the curing time is 6 s.

The prepared composition is introduced in polypropylene contact lens molds (+6.00 D) and irradiated with a UV radiation at an intensity of about 16 mW/cm$^2$ (intensity weighted by the normalized initiator master spectrum), which is from a Hamamatsu UV Lamp with a 330 nm cut-off filter after the condenser unit, for about 30 seconds. The molded silicone contact lenses (or silicone rubber contact lenses) are extracted with Methyl Ethyl Ketone (MEK) for 6 minutes and then hydrated in water. The lenses are packed in PBS for autoclaving. The hydrated contact lenses are determined to have the following properties: an oxygen permeability (Dk) is greater than 1000 barrers (beyond the upper measurement limit of the instrument); non-detectable ion permeability; an elastic modulus (Young's modulus) of about 1.46 MPa; an elongation at break of about 164%; a diameter of 14.49 mm, a water content of about 1.02% by weight, and a swelling ratio of 52% in toluene.

EXAMPLE 3

A clear polymerizable silicone composition is prepared to have 75% by weight of α,ω-bis(diacrylamidopropyl)-polydimethylsiloxane (Mw~7500), 24% by weight of 1-propanol, and 1% by weight of a photoinitiator Darocur® 1173 (Ciba). Soft silicone contact lenses are produced by photopolymerization of the prepared composition in plastic molds according to the procedures described in Example 2. Photo-rheology study is carried out to determine cure time and the shear storage modulus (kPa). The shear storage modulus (G') is 250 kPa and the curing time is 10 s.

The prepared composition is introduced in polypropylene contact lens molds (+6.00 D) and irradiated with a UV radiation at an intensity of about 16 mW/cm$^2$, which is from a Hamamatsu UV Lamp with a 330 nm cut-off filter after the condenser unit, for about 1.5 minutes. The molded silicone contact lenses (or silicone rubber contact lenses) are extracted with MEK for 6 minutes and then hydrated in water. The lenses are packed in PBS for autoclaving. The hydrated silicone contact lenses are determined to have the following properties: an oxygen permeability (Dk) is greater than 1000 barrers (beyond the upper measurement limit of the instrument); non-detectable ion permeability; an elastic modulus (Young's modulus) of about 0.83 MPa; an elongation at break of about 197%; a diameter of 13.03 mm, a water content of about 1.16% by weight, and a swelling ratio of 44% in toluene.

EXAMPLE 4

Various polymerizable silicone compositions listed in Table 1 are prepared from the following components: Am-PDMS-Am: α,ω-bis(diacrylamidopropyl)-polydimethylsiloxane (Mw~7500); MRS-044: (methacryloxypropyl)methylsiloxane; Tris-Am: N-[tris(trimethylsiloxy)-silylpropyl] acrylamide; MA-PEG-OCH$_3$ 480: polyethylene glycol methyl ether methacrylate (Mw~480); MA-PEG-OH 360: polyethylene glycol methacrylate (Mw~360); 1-PrOH: 1-propanol.

TABLE 1

|  | Composition No. | | | | | |
| --- | --- | --- | --- | --- | --- | --- |
|  | 5-0 | 5-1 | 5-2 | 5-3 | 5-4 | 5-5 |
| Am-PDMS-Am 7500 | 75% | 64% | 37.5% | 56% | 74% | 74% |
| MRS-044 | — | 11% | 37.5% | — | — | — |
| Tris-Am | — | — | — | 19% | — | — |
| MA-PEG-OCH$_3$ 480 | — | — | — | — | 1% | — |
| MA-PEG-OH 360 | — | — | — | — | — | 1% |
| 1-PrOH | 24% | 24% | 24% | 24% | 24% | 24% |
| Darocur 1173 | 1% | 1% | 1% | 1% | 1% | 1% |

Soft contact lenses are produced by photopolymerization of a composition in plastic molds according to the procedures described in Example 3. The molded silicone contact lenses are extracted with methyl ether ketone (MEK) for 6 minutes and then hydrated in water. The lenses are packed in PBS for autoclaving. The hydrated silicone contact lenses are determined to have an oxygen permeability of greater than 1000 barrers (beyond the upper measurement limit of the instrument), a non-detectable ion permeability (below the detection limit), and other properties reported in Table 2.

TABLE 2

|  | Lenses molded from Composition No. | | | | | |
| --- | --- | --- | --- | --- | --- | --- |
| Properties | 5-0 | 5-1 | 5-2 | 5-3 | 5-4 | 5-5 |
| Elastic modulus (MPa) | 0.83 | 0.75 | 0.72 | 0.71 | 0.78 | 0.67 |
| Elongation at break | 197% | 168% | 182% | 241% | 203% | 272% |
| Diameter (mm) | 13.03 | 12.89 | 13.05 | 13.06 | 13.07 | 13.12 |
| % H$_2$O | 1.16 | 1.6 | 3.5 | 13.1 | 1.9 | 2.1 |
| Swelling ratio in 2-propanol | 9% | 14% | 13% | 12% | 13% | 14% |
| Swelling ratio in MEK | 19% | 24% | 33% | 30% | 32% | 30% |
| Swelling ratio in toluene | 44% | 52% | 56% | 52% | 63% | 62% |

EXAMPLE 5

Photo-Curing

Various polymerizable silicone compositions listed in Table 3 are prepared from the following components: PDMS$_{11,500}$-bisAm: α,ω-bis(diacrylamidopropyl)-polydimethylsiloxane (Mw~11,500 Daltons); PDMS$_{7,500}$-bisAm: α,ω-bis(diacrylamidopropyl)-polydimethylsiloxane (Mw~7500 Daltons); Darocur® 1173 (Ciba).

TABLE 3

| | Composition (% by weight) | | |
|---|---|---|---|
| | Formulation A | Formulation B | Formulation C |
| $PDMS_{11,500}$-BisAm | 99 | 49.5 | — |
| $PDMS_{7500}$-BisAm | — | 49.5 | 99 |
| Darocur 1173 | 1 | 1 | 1 |

Photo-rheology studies of the polymerizable silicone compositions are carried out to determine cure time and the shear storage modulus (kPa). The shear storage modulus (G') is reported in Table 4 and can give an estimation of the lens tensile modulus (E'). The curing UV light source is a mercury bulb that emits in the 325 to 370 nm wavelength range at an intensity of 10 mW/cm² (intensity weighted by the normalized initiator master spectrum).

A polymerizable silicone composition prepared above is introduced into polypropylene lens molds and cured at room temperature (RT) for a curing time listed in Table 4 with the UV light source used for photorheology study. The properties of the obtained silicone contact lenses are reported in Table 4. In all 3 UV cured formulations, the cure time is less than 20 seconds and the cure temperature is room temperature. However, the modulus values are too high. This can be improved by increasing the molecular weight of the macromers. The elongation to break is also rather low.

TABLE 4

| | Hydro-silylation Curing | UV Curing | | |
|---|---|---|---|---|
| | | Formulation A | Formulation B | Formulation C |
| Cure temperature (° C.) | 120° C. | RT | RT | RT |
| Cure Time | 2 hours | 13 s | 15 s | 15 s |
| G' (kPa) | NA | 340 | 390 | 420 |
| Modulus (MPa) | 1.1 | 1.1 | 1.2 | 1.4 |
| Elongation to Break (%) | 170 | 110 | 100 | 80 |

EXAMPLE 6

Elongation to break is used to estimate lens toughness and is affected by quality of the cross-linked network in the lens. Improvements in the network should increase the elongation to break. Defects such as dangling ends, network loops, and inhomogeneous crosslinking site distribution all can lead to diminished network properties, such as elongation to break.

This Example illustrates use of polydimethylsiloxane having two terminal thiol groups to improve network mechanical properties.

Various polymerizable silicone compositions listed in Table 5 are prepared from the following components: $PDMS_{11,500}$-bisAm: α,ω-bis(diacrylamidopropyl)-polydimethylsiloxane (Mw~11,500 Daltons); $PDMS_{7,500}$-bisAm: α,ω-bis(diacrylamidopropyl)-polydimethylsiloxane (Mw~7500 Daltons); $PDMS_{3000}$-bis-SH: α,ω-bis(thiolpropyl)-polydimethylsiloxane (Mw~3000 Daltons); $PDMS_{6000}$-bis-SH: α,ω-bis(thiolpropyl)-polydimethylsiloxane (Mw~6000 Daltons); $PDMS_{12000}$-bis-SH: α,ω-bis(thiolpropyl)-polydimethylsiloxane (Mw~12000 Daltons); Darocur® 1173 (Ciba).

TABLE 5

| | Composition of formulation (% by weight) | | | |
|---|---|---|---|---|
| | Control | B1 | B2 | B3 |
| $PDMS_{11,500}$-BisAm | 49.5 | 46.16 | 46.16 | 46.16 |
| $PDMS_{7,500}$-BisAm | 49.5 | 46.16 | 46.16 | 46.16 |
| $PDMS_{3000}$-Bis-SH | — | 6.68 | — | — |
| $PDMS_{6000}$-Bis-SH | — | — | 6.68 | — |
| $PDMS_{12000}$-Bis-SH | — | — | — | 6.68 |
| Darocur 1173 (%) | 1 | 1 | 1 | 1 |
| $R_{Am/SH}$ [#] | — | 4.46 | 9.15 | 18.14 |

[#] Molar ratio of the concentration of acryloylamido group over the concentration of thiol group Table 6 shows the effect of the addition of 6.67% Bis-SH PDMS of different molecular weights upon the UV curing of polymerizable silicone compositions, as examined in photo-rheology study which is performed according to the procedures described in Example 5. The cure times have now decreased from about 15 seconds to about 7 seconds and the G' values have decreased from 390 to 250-300 kPa. These G' values should translate to a tensile modulus of 0.75 to 0.9 MPa. It is observed that the G' does not reach the plateau value for the sample with the 3000 molecular weight. It may be due to the presence of an excess of thiols that further crosslink after the double bonds have been completely consumed.

TABLE 6

| | Control | B1 | B2 | B3 |
|---|---|---|---|---|
| Cure temperature | RT | RT | RT | RT |
| Cure Time (s) | 15 | 5 | 7 | 5 |
| G' (kPa) | 390 | 250 | 300 | 300 |

EXAMPLE 7

Cure times of 5 or 7 seconds could be too fast for optimal lens properties. This Example illustrates how to adjust the curing time with the addition of bismethacryloyloxy-terminated PDMS (PDMS-BisMa).

Various formulations (polymerizable silicone compositions) are prepared to have varied concentrations of $PDMS_{6000}$-Bis-SH along with $PDMS_{11500}$-BisAm, and $PDMS_{10,000}$-BisMa using a mixture DOE (Design of Experiment). The photo-rheology study and lens curing are performed according to the procedures described in Example 5. The formulation compositions, photo-rheology data and lens properties are shown in Table 7.

TABLE 7

| | Formulation | | | | |
|---|---|---|---|---|---|
| | C | D | E | F | G |
| $PDMS_{6000}$-Bis-SH (%) | 0 | 6 | 3 | 12 | 3 |
| $PDMS_{11,500}$-BisAm (%) | 83 | 78 | 75 | 78 | 75 |
| $PDMS_{10,000}$-BisMa (%) | 16 | 15 | 21 | 12 | 12 |
| Darocur 1173 (%) | 1 | 1 | 1 | 1 | 1 |
| $R_{(Am+Ma)/SH}$ [#] | — | 11.70 | 3.33 | 7.33 | 5.83 |
| Cure time by Photorheology(s) | 46 | 27 | 45 | 31 | 29 |
| G' (kPa) | 320 | 260 | 250 | 240 | 270 |
| Lens cure time (s) * | 58 | 34 | 56 | 46 | 41 |

TABLE 7-continued

| | Formulation | | | | |
|---|---|---|---|---|---|
| | C | D | E | F | G |
| Lens Modulus (MPa) | 0.76 | 0.76 | 0.72 | 0.75 | 0.75 |
| Lens Elongation to Break (%) | 150 | 290 | 325 | 370 | 285 |

\* lens cure times were 25% higher than the cure time by photo-rheology to prevent possible under curing.
Molar ratio of the concentration sum of acryloylamido and methacryloyloxy groups over the concentration of thiol group The results in Table 7 indicate that the addition of $PDMS_{10000}$-BisMa can increase the curing time to a desirable 27 to 46 seconds while maintaining the favorable lens modulus and elongation to break values, that the addition of $PDMS_{6000}$-Bis-SH can increase significantly the lens elongation to break from 150% to an average of about 317% while maintaining the lens modulus, and that the mechanical properties of lenses are not varied significantly with the molar ratio of (meth)acryloyl concentration (i.e., the concentration sum of acryloylamido and methacryloyloxy groups here) over thiol concentration.

What is claimed is:

1. A method for producing a silicone medical device, comprising the steps of:
    (1) obtaining a polymerizable silicone composition which comprises
        (a) (i) from about 70% to about 97% by weight of one or more first polydiorganosiloxanes each having at least two (meth)acryloylamido groups, and (ii) from about 2% to about 15% by weight of one or more second polydiorganosiloxanes each having at least two (meth)acryloyloxy groups, wherein each of the first and second polydiorganosiloxanes has an averaged molecular weight of at least about 2000 Daltons,
        (b) from about 1.0% to about 20.0% by weight of one or more third polydiorganosiloxanes each having at least two thiol groups and an averaged molecular weight of at least about 2000 Daltons, and
        (c) from about 0.1% to about 3% by weight of a free-radical initiator,
        provided that components (a) to (c) listed above and any additional polymerizable components present in the polymerizable silicone composition add up to 100% by weight;
    (2) introducing the polymerizable silicone composition into a mold for making a silicone medical device; and
    (3) curing thermally or actinically the polymerizable silicone composition in the mold to form the silicone medical device,
    wherein the formed silicone medical device has an elastic modulus of about 1.2 MPa or less and an elongation at break of about 200% or larger.

2. The method of claim 1, wherein the first, second, and third polydiorganosiloxanes independent of one another are a linear polydiorganosiloxane.

3. The method of claim 1, wherein the first, second, and third polydiorganosiloxanes independent of one another are a linear polydimethylsiloxane.

4. The method of claim 3, wherein the free-radical initiator is a thermal initiator.

5. The method of claim 3, wherein the free-radical initiator is a photoinitiator.

6. The method of claim 5, wherein the polymerizable silicone composition comprises a UV-absorbing vinylic monomer.

7. The method of claim 1, wherein the medical device is a silicone contact lens.

8. The method of claim 2, wherein the polymerizable silicone composition comprises from about 75% to about 95% by weight of the first polydiorganosiloxanes.

9. The method of claim 2, wherein the polymerizable silicone composition comprises from about 80% to about 93% by weight of the first polydiorganosiloxanes.

10. The method of claim 1, wherein the first and second polydiorganosiloxanes independent of one another have an average molecular weight of from about 6000 to about 200000 Daltons.

11. The method of claim 8, wherein the first and second polydiorganosiloxanes independent of one another have an average molecular weight of from about 6000 to about 200000 Daltons.

12. The method of claim 9, wherein the first and second polydiorganosiloxanes independent of one another have an average molecular weight of from about 6000 to about 200000 Daltons.

13. The method of claim 10, wherein the third polydiorganosiloxanes have an average molecular weight of from about 4000 to about 150000 Daltons.

14. The method of claim 11, wherein the third polydiorganosiloxanes have an average molecular weight of from about 4000 to about 150000 Daltons.

15. The method of claim 12, wherein the third polydiorganosiloxanes have an average molecular weight of from about 4000 to about 150000 Daltons.

16. The method of claim 6, wherein the first and second polydiorganosiloxanes independent of one another have an average molecular weight of from about 6000 to about 200000 Daltons, wherein the third polydiorganosiloxanes have an average molecular weight of from about 4000 to about 150000 Daltons.

17. The method of claim 6, wherein the polymerizable silicone composition comprises from about 75% to about 95% by weight of the first polydiorganosiloxanes, wherein the first and second polydiorganosiloxanes independent of one another have an average molecular weight of from about 6000 to about 200000 Daltons, wherein the third polydiorganosiloxanes have an average molecular weight of from about 4000 to about 150000 Daltons.

18. The method of claim 6, wherein the polymerizable silicone composition comprises from about 80% to about 93% by weight of the first polydiorganosiloxanes, wherein the first and second polydiorganosiloxanes independent of one another have an average molecular weight of from about 6000 to about 200000 Daltons, wherein the third polydiorganosiloxanes have an average molecular weight of from about 4000 to about 150000 Daltons.

19. The method of claim 18, wherein the medical device is a silicone contact lens.

\* \* \* \* \*